(12) United States Patent
    Ilmoniemi et al.

(10) Patent No.: US 11,167,147 B2
(45) Date of Patent: Nov. 9, 2021

(54) CONTROL OF TRANSCRANIAL MAGNETIC STIMULATION

(71) Applicant: Aalto-korkeakoulusäätiö, Aalto (FI)

(72) Inventors: Risto Ilmoniemi, Helsinki (FI); Jaakko Nieminen, Helsinki (FI); Lari Koponen, Espoo (FI)

(73) Assignee: Aalto-korkeakoulusäätiö, Aalto (FI)

( * ) Notice: Subject to any disclaimer, the term of this patent is extended or adjusted under 35 U.S.C. 154(b) by 119 days.

(21) Appl. No.: 16/500,566

(22) PCT Filed: Apr. 3, 2018

(86) PCT No.: PCT/FI2018/050238
§ 371 (c)(1),
(2) Date: Oct. 3, 2019

(87) PCT Pub. No.: WO2018/185369
PCT Pub. Date: Oct. 11, 2018

(65) Prior Publication Data
US 2020/0101308 A1     Apr. 2, 2020

(30) Foreign Application Priority Data
Apr. 3, 2017   (FI) .................................... 20175309

(51) Int. Cl.
    *A61N 2/02*      (2006.01)
    *A61N 2/00*      (2006.01)
(52) U.S. Cl.
    CPC .............. *A61N 2/006* (2013.01); *A61N 2/02* (2013.01)

(58) Field of Classification Search
    CPC .................................. A61N 2/006; A61N 2/02
    See application file for complete search history.

(56) References Cited

U.S. PATENT DOCUMENTS

| 2003/0032852 | A1  | 2/2003 | Perreault et al. |
| 2008/0200748 | A1* | 8/2008 | Testani ............ A61N 2/004 600/13 |
| 2010/0152522 | A1  | 6/2010 | Roth et al. |

FOREIGN PATENT DOCUMENTS

| EP | 1894600 A1 | 3/2008 |
| GB | 2298370 A  | 9/1996 |

(Continued)

OTHER PUBLICATIONS

Search Report issued by the Finnish Patent and Registration Office in Finnish Application No. 20175309 dated Oct. 24, 2017. 2 pages.

(Continued)

*Primary Examiner* — Christine H Matthews
(74) *Attorney, Agent, or Firm* — Meunier Carlin & Curfman LLC

(57) ABSTRACT

The invention relates to a transcranial magnetic stimulation device comprising: at least two coils, an input channel for each coil, a control unit, and at least one energy storage for storing energy for the at least two coils, the control unit being configured to: determine at least one stimulus intensity; determine an energy level stored in the at least one energy storage; determine a modulation pattern for each coil; and generate at least one control signal for controlling the input channel of the at least one coil of the at least two coils according to the determined modulation pattern in order to control an input of each coil from the at least one energy storage. A method is also disclosed.

11 Claims, 7 Drawing Sheets

(56) References Cited

FOREIGN PATENT DOCUMENTS

| WO | 2006134598 | A2 | 12/2006 |
| WO | 2009026386 | A1 | 2/2009 |
| WO | 2010135425 | A1 | 11/2010 |

OTHER PUBLICATIONS

International Search Report and Written Opinion issued by the International Searching Authority (EPO) in PCT Application No. PCT/FI2018/050238 dated Jun. 8, 2018. 12 pages.

* cited by examiner

CONTROL OF TRANSCRANIAL MAGNETIC STIMULATION

CROSS-REFERENCE TO RELATED APPLICATIONS

This application is a national stage application, filed under 35 U.S.C. § 371, of PCT/FI2018/050238, filed Apr. 3, 2018, which claims the benefit of and priority to Finnish Patent Application No. 20175309, filed Apr. 3, 2017, the disclosures of which are expressly incorporated herein by reference in their entirety.

TECHNICAL FIELD

The invention concerns in general the technical field of transcranial magnetic stimulation. More particularly, the invention concerns controlling of transcranial magnetic stimulation.

BACKGROUND

Transcranial magnetic stimulation (TMS) is a noninvasive tool for stimulating cortical neurons. TMS is used, e.g., for presurgical mapping of functional areas of the cortex, studying the cortical effective connectivity, and treatment of major depression.

In TMS, the stimulation is achieved by feeding a brief, strong current pulse through the windings of a coil placed over the subject's scalp. This causes a time-varying magnetic field that induces an electric field in the cortex, resulting in membrane de- and hyperpolarization in the targeted neurons.

In multichannel TMS (mTMS), the stimulator coil unit consists of several coils that can be controlled independently. The electric field (E-field) pattern induced in the brain can be modified by adjusting the current passing through the windings of each individual coil. The total E-field is the sum of the E-fields produced by the individual coils, each E-field intensity being proportional to the rate of change of the coil current of the individual coil. Because the E-field determines the site of stimulation, mTMS allows controlling the stimulus location electronically without the need to move the coil unit.

In mTMS, the speed by which the stimulus pattern (E-field) can be controlled is a key parameter that determines for what kind of use the device is suitable for. Having the possibility to change the stimulus within approximately a millisecond or several milliseconds is needed in some paradigms. For example, in a conventional single-channel paired-pulse TMS paradigm, two TMS pulses with independently controlled intensities are delivered only 2-5 ms apart. Preferably, an mTMS device should be able to deliver these two pulses in different locations—or even better, be able to deliver an arbitrary pulse train with a desired spatial—temporal pattern.

The E-field intensity, which is proportional to the rate of change of the coil current, is proportional to the voltage of the charge-storage capacitor (or a capacitor bank, consisting of capacitors in parallel and/or in series). Thus, in order to change the stimulus intensity or stimulus location in mTMS, the voltage levels of the capacitors need to be adjusted quickly. However, depending on the capacitance, the capacitor charger, or the discharge mechanism, the voltage-level adjustment may take from tens of milliseconds up to a few seconds. In conventional single-channel paired-pulse TMS devices, the speed issue is commonly overcome by having two capacitors that can be charged independently before the stimulation: one of the capacitors is used for the first pulse and the other for the second pulse. However, this increases the cost and the size of the device. Furthermore, delivering more than two independent pulses with short intervals would require adding even more capacitors. In some mTMS paradigms, the stimulus locations and intensities may not even be known in advance, e.g., when a feedback-controlled system is in use, making it impractical to fix the capacitor voltages before the pulse sequence. One simple example in which a fast, impossible-to-design-in-advance intensity adjustment is needed is the case when the relative movement of the coil and the brain is compensated for by adjusting the coil currents accordingly.

Moreover, the conventional solutions have a drawback that the pulse duration depends on the inductance of the coil, which has made it challenging to adapt the stimulus pulse individually. For solving this, there are introduced solutions in which the current input to the coil is controlled through a modulated control signal of the power source inputting the current to the coil. In this manner, it is possible to adjust the waveform of the current input to the coil and, hence, the E-field induced in the brain. This kind of prior art solutions are still facing the drawbacks as discussed above i.e. they are based on one coil only, and further they are capacitor-coil specific and, as a result, the cost and size of the TMS device remains high.

As may be seen from above, the prior art solutions have drawbacks and there is a need to mitigate the drawbacks by introducing new approaches for controlling the generation of the pulses for TMS.

SUMMARY

The following presents a simplified summary in order to provide basic understanding of some aspects of various invention embodiments. The summary is not an extensive overview of the invention. It is neither intended to identify key or critical elements of the invention nor to delineate the scope of the invention. The following summary merely presents some concepts of the invention in a simplified form as a prelude to a more detailed description of exemplifying embodiments of the invention.

An objective of the invention is to present a transcranial magnetic stimulation device and a method for controlling a generation of magnetic field by the transcranial magnetic device. Another objective of the invention is that the transcranial magnetic stimulation device and the method enable controlling of an input of the coils of the transcranial magnetic stimulation device.

The objectives of the invention are reached by a transcranial magnetic stimulation device and a method as defined by the respective independent claims.

According to a first aspect, a transcranial magnetic stimulation device comprising: at least two coils, an input channel for each coil, a control unit and at least one energy storage for storing energy for the at least two coils is provided wherein the control unit is configured to: determine at least one stimulus intensity intended to be generated in the target by generating magnetic field by at least one coil of the at least two coils; determine an energy level stored in the at least one energy storage; determine a modulation pattern for each coil for generating the magnetic field by the at least one coil of the at least two coils, the generated magnetic field by the at least one coil causing the intended stimulus intensity in the target; generate at least one control signal for controlling the input channel of the at least one coil of the at least two coils according to the determined modulation pattern in order to control an input of each coil from the at least one energy storage.

The at least one energy storage may be arranged in one of the following manner: at least one common energy storage for a plurality of the coils, at least one dedicated energy storage for each coil, at least one common energy storage for a plurality of the coils and at least one dedicated energy storage for each coil, at least one common energy storage for a plurality of coils and at least one dedicated energy storage for at least one coil.

The at least one energy storage may comprise at least one capacitor.

The control unit may further be configured to determine the energy level stored in the at least one energy storage by measuring a voltage level of the at least one energy storage.

The control unit may also be configured to, in response to a detection that the energy level stored in the at least one energy storage is below an energy level needed for generating a magnetic field with the at least one coil causing the intended stimulus intensity in the target with the determined modulation pattern, initiate a charging of the at least one energy storage.

Further, the control unit may be configured to determine the modulation pattern for generating a plurality of consecutive magnetic fields with the at least one coil.

The generated at least one control signal may be configured to control a conductive state of at least one switching device in at least one input channel. For example, the switching device may be at least one of the following: insulated-gate bipolar transistor, IGBT; metal-oxide-semiconductor field-effect transistor, MOSFET.

The control unit may be configured to control the input of each coil with a pulse-width-modulation-based control signal.

The control unit may also be configured to control the input of each coil in a step-like manner.

According to a second aspect, a method for controlling an input of a plurality of coils of a transcranial magnetic stimulation device is provided, the device comprising: at least two coils, an input channel for each coil, a control unit, at least one energy storage for storing energy for the at least two coils, wherein the method comprises: determining at least one stimulus intensity intended to be generated in the target by generating magnetic field by at least one coil of the at least two coils; determining an energy level stored in the at least one energy storage; determining a modulation pattern for each coil for generating the magnetic field by the at least one coil of the at least two coils, the generated magnetic field by the at least one coil causing the intended stimulus intensity in the target; generating at least one control signal for controlling the input channel of the at least one coil of the at least two coils according to the determined modulation pattern in order to control an input of each coil from the at least one energy storage.

Various exemplifying and non-limiting embodiments of the invention both as to constructions and to methods of operation, together with additional objects and advantages thereof, will be best understood from the following description of specific exemplifying and non-limiting embodiments when read in connection with the accompanying drawings.

The verbs "to comprise" and "to include" are used in this document as open limitations that neither exclude nor require the existence of unrecited features. The features recited in dependent claims are mutually freely combinable unless otherwise explicitly stated. Furthermore, it is to be understood that the use of "a" or "an", i.e. a singular form, throughout this document does not exclude a plurality.

BRIEF DESCRIPTION OF FIGURES

The embodiments of the invention are illustrated by way of example, and not by way of limitation, in the figures of the accompanying drawings.

DESCRIPTION OF THE EXEMPLIFYING EMBODIMENTS

The specific examples provided in the description given below should not be construed as limiting the scope and/or the applicability of the appended claims. Lists and groups of examples provided in the description given below are not exhaustive unless otherwise explicitly stated.

Figure 1:
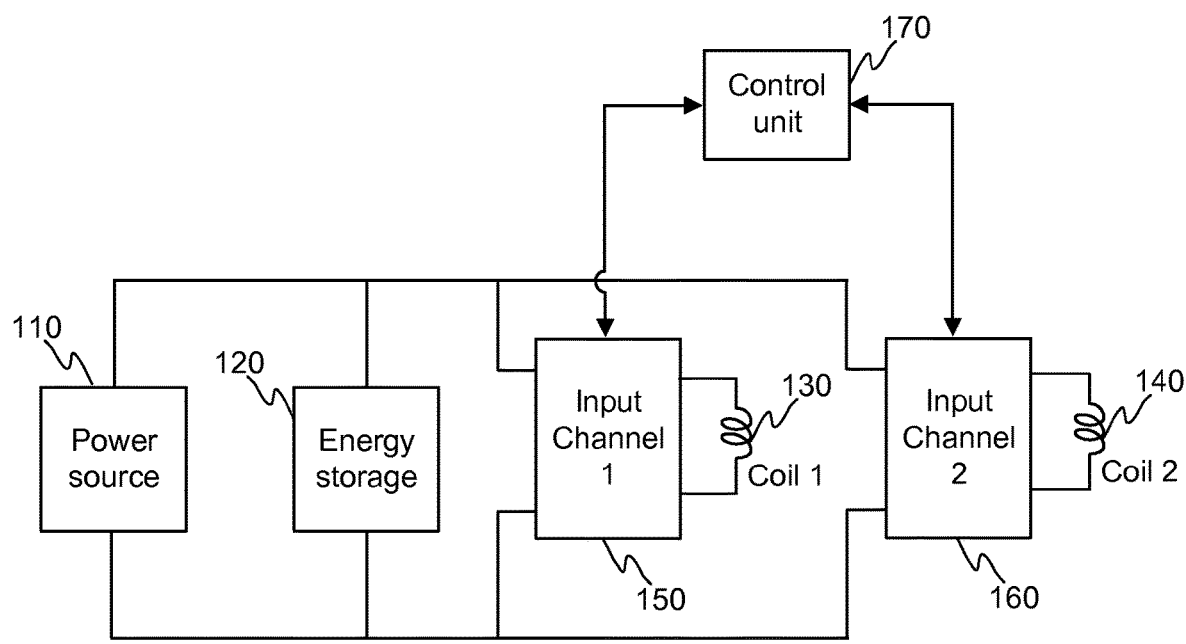
FIG. 1 schematically illustrates at least some aspects of a principle of the invention.

FIG. 1 schematically illustrates at least some aspects of a principle of the present invention applied in a field of a multichannel transcranial magnetic stimulation wherein the stimulator coil unit consists of several coils 130, 140 that can be controlled independently. The electric field (E-field) pattern induced in a target may be modified by adjusting the current passing through the windings of each individual coil. According to FIG. 1, at least a selection of the coils 130, 140 may be performed by controlling the input channels 150, 160 of the corresponding coils 130, 140 by a control unit 170. As schematically illustrated in FIG. 1 circuit energy is fed by a power source 110, which is stored in energy storage 120 to be supplied to the coils 130, 140 in a controlled manner. The energy storage 120 is, according to invention non-limiting example as illustrated in FIG. 1, common to at least two coils 130, 140. FIG. 1 is illustrated with two coils 130, 140, but the number of coils is not limited to two. The input channels may comprise a number of switching devices on one side or both sides of the coil in question.

The present invention is at least in part based on an idea that the control unit 170 may be configured to determine at least one stimulus intensity to be caused by an electric field induced in a target in response to a generation of the magnetic field by at least one of the coils 130, 140 and control a generation of the magnetic field by the coil 130, 140 in question accordingly. The controlling may be arranged so that the control unit 170 is configured to determine an energy level of the energy storage 120 dedicated to the coil in question or common to a plurality of coils, or even a combination of these two. The determination may e.g. be performed so that the control unit 170 may comprise, or is coupled to, a measurement arrangement by means of which it is possible to measure a voltage of the energy storage or energy storages, such as a capacitor or capacitors, in question. Additionally, the determination may comprise predetermined calculation by means of which the described piece of information may be derived. Moreover, the control unit 170 may be configured to determine a modulation pattern for each coil for generating the magnetic field by the at least one coil 130, 140 of the at least two coils 130, 140 wherein the generated magnetic field by the at least one coil causes the intended stimulus intensity in the target. The determination of modulation pattern may also comprise a step of detecting whether the energy storages have necessary amount of energy in order to generate the magnetic field through the modulation. In some embodiment, if it is detected that the store energy is not high enough for generating the magnetic field, the control unit may be configured to initiate the charging of the number of energy storages prior to continuing the procedure further. The initiation may e.g. comprise a generation a control signal to the power source 110 in order to provide current to the energy storage. At the same time, any controlling to the input channels may be prevented. In some other embodiment the control unit 170 may be configured to obtain a limit set for an energy level to an energy storage or energy storages and to monitor that the limit is reached when the one or more energy storages are charged before enabling to perform the solution according to the present invention. Moreover, in some embodiment, the control unit may be configured to determine the modulation pattern for generating a plurality of consecutive magnetic fields with the at least one coil 130, 140. In response to the determination, the control unit 170 may be configured to generate at least one control signal for controlling the input channel of the at least one coil 130, 140 of the at least two coils 130, 140 according to the determined modulation pattern in order to control an input of each coil 130, 140 from the at least one energy storage 120. Hence, the generated control signal may be at least in part dependent on the energy level stored in the at least one energy storage and the aim is to generate such an input signal to the coil in question, which causes a generation of the desired stimulus intensity in the target. In other words, input to the coil 130, 140 in question through the input channel is advantageously in a form of a current pulse which is modulated by the control unit 170 through controlling an input channel 150, 160 accordingly. By controlling the input channels 150, 160 it is possible to generate an individually modulated input current, i.e. input signal, for each coil 130, 140 and in that manner to control the induced E-field in the target.

The energy storage 120 may refer to a device, or a plurality of devices coupled to each other, which may store energy. The storing of energy may be arranged so that the power source provides electrical energy to the energy storage 120, which electrical energy may be stored through charging of the electrical energy. An applicable device for storing energy in the application area may be a charge-storage capacitor, or a capacitor bank, which may be charged and discharged. Naturally, the capacitor, or the plurality of capacitors, shall be selected so that their operating parameters meet the need in the application area. As mentioned, the energy storage 120 is arranged in the circuit so that it may provide the stored energy to a plurality of coils 130, 140.

The input channel 150, 160, in turn, may comprise a number of switching devices by means of which a coil 130, 140 into which the energy from the energy storage 120 is to be input, but also by means of which the input current pulse may be modulated. In other words, by controlling at least one switch the mentioned effects may be achieved. The switching devices belonging to the input channel 150, 160 may e.g. be insulated-gate bipolar transistors (IGBT) which are power semiconductor devices primarily used as an electronic switch. One advantage of IGBT devices is that they combine high efficiency and fast switching, which makes them applicable in the area of transcranial magnetic stimulation. The controlling of the IGBT is arranged by applying a control voltage to the metal-oxide-semiconductor gate structure, which drives the IGBT to conducting state, or vice versa. Another example of an applicable switching device is a metal-oxide-semiconductor field-effect transistor (MOSFET). The input channel 150, 160 may comprise a necessary number of switching devices coupled to each other in a way that the selection of the coils 130, 140 may be achieved as well as the modulation may be performed to the current pulse to be input to the selected coil 130, 140.

The control unit 170 may refer to a device comprising a processing unit and a memory unit wherein a computer program code is stored in the memory unit. The computer program code, when executed by the processing unit, generates instructions for controlling an operation of the control unit 170, and hence the device for stimulating the target with a magnetic field generated by the coil, or coils. The control unit 170 may also store instructions regarding the magnetic field(s) to be generated with the device, i.e. with the coils belonging to the device. For example, the information regarding the magnetic fields may be pre-stored in the memory or be generated e.g. in response to a feedback signal obtained e.g. from the target for which the magnetic field is generated for inducing the electric field in the target. For example, in case the target is a human brain the feedback signal may be obtained by monitoring electric currents in brain in response to the induction of the electric field in the target, and in response to that to generate information, or instructions, in the control unit 170. Alternatively, in some application area the feedback signal may be obtained by monitoring an electrical activity of one or more muscles in response to inducing the electric field in a target as described. The feedback signal in such an implementation may e.g. be obtained with an electromyography or with applicable acceleration sensors position on a target surface. The control unit 170, thus, generates a control signal for selecting a coil 130, 140, and for modulating the signal to be input to the selected coil 130, 140 in order to achieve a desired effect in the target. Naturally, the control unit 170 may receive its power from a power source and may comprise further elements and/or units coupled to it, such as a measurement device for obtaining information on an energy level of at least one energy storage. These are not described in more detail in this context.

Figure 2:
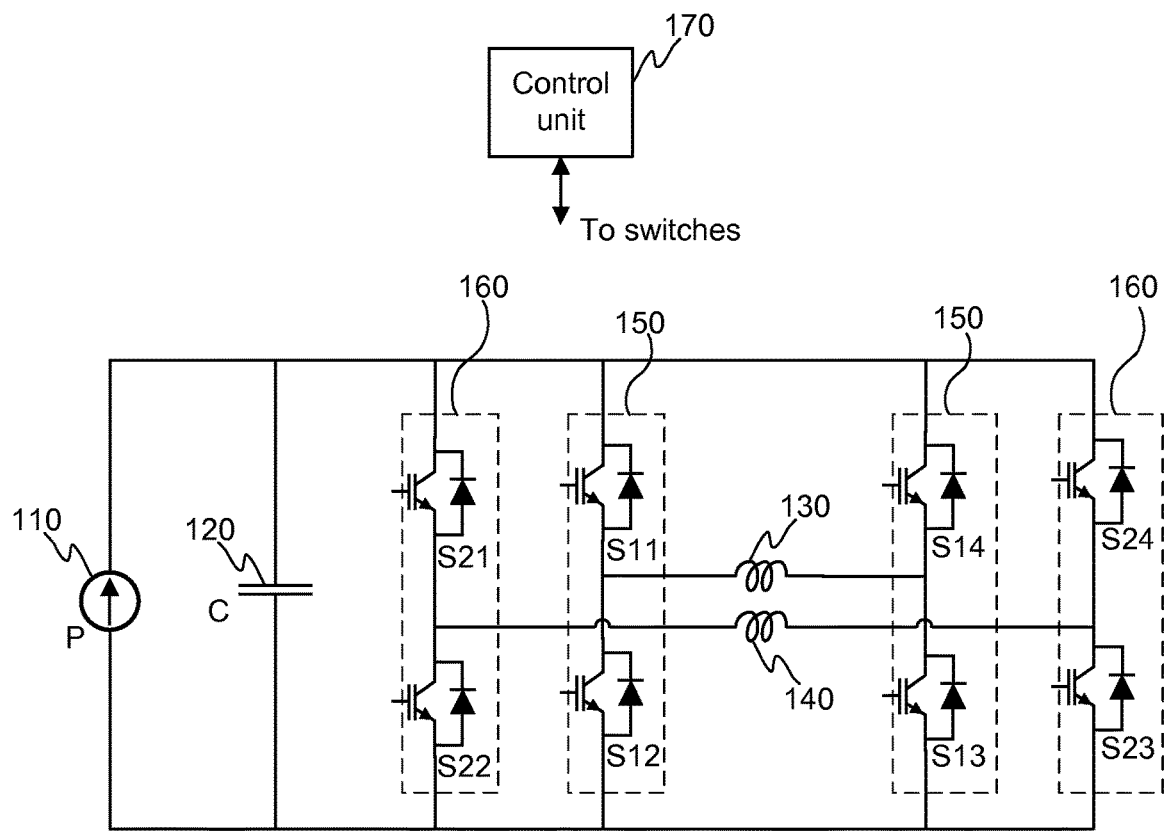
FIG. 2 schematically illustrates an example of a solution according to an embodiment of the invention.

Next, it is discussed on the device for a multichannel transcranial magnetic stimulation as schematically illustrated in FIG. 2 as an example of a solution according to an embodiment of the present invention. In FIG. 2, it is disclosed an example of an implementation of the device on a component level. The device as depicted in FIG. 2 comprises a power source 110 for providing electrical energy for energy storage 120, which in the implementation of FIG. 2 is a capacitor C. The capacitor is coupled with respect to coils 130, 140 in such a manner that the same capacitor may provide electrical energy to both of the coils 130, 140 through a corresponding input channel 150, 160. The input channel 150 may comprise a plurality of controllable switching components which are Insulated-gate bipolar transistors in the implementation of the FIG. 2. In order to select the coil 130 and to generate and supply input current pulses therein IGBTs referred with S11, S12, S13 and S14 may be controlled by providing applicable control signals to the gates of the mentioned IGBTs. The IGBTs S11, S12, S13 and S14 are rounded with boxes representing an input channel 150 for the coil 130 in FIG. 2. Similarly, in order to select the other coil 140 and to generate and supply input current pulses therein IGBTs referred with S21, S22, S23 and S24 may be controlled by providing applicable control signals to the gates of the mentioned IGBTs. The IGBTs S21, S22, S23 and S24 are rounded with boxes representing an input channel 160 for the coil 140 in FIG. 2. The control signals to the gates of the IGBTs may be generated in the control unit 170, wherein the selection between the coils 130, 140 to be supplied is determined under predetermined scheme and the control signals may be generated for the IGBTs in order to modulate the current obtained from the common energy storage 120. In order to generate the control signals the control unit may receive, as input, information on a coil 130, 140 by means of which the magnetic field shall be generated. Additionally, the control unit 170 may receive information representing charging status of the energy storage 120. By means of the mentioned pieces of information the control unit 170 may generate a modulation scheme for the current obtained from the energy storage 120 in order to generate a current pulse to the selected coil 130, 140, which generates a magnetic field for inducing a desired electrical field in the target. The control signals to the gates of the IGBTs, or the controlling of the switching devices in general, may advantageously be implemented with dedicated signal channels between the control unit 170 and the IGBT, or the switching device, in question.

Figure 3A:
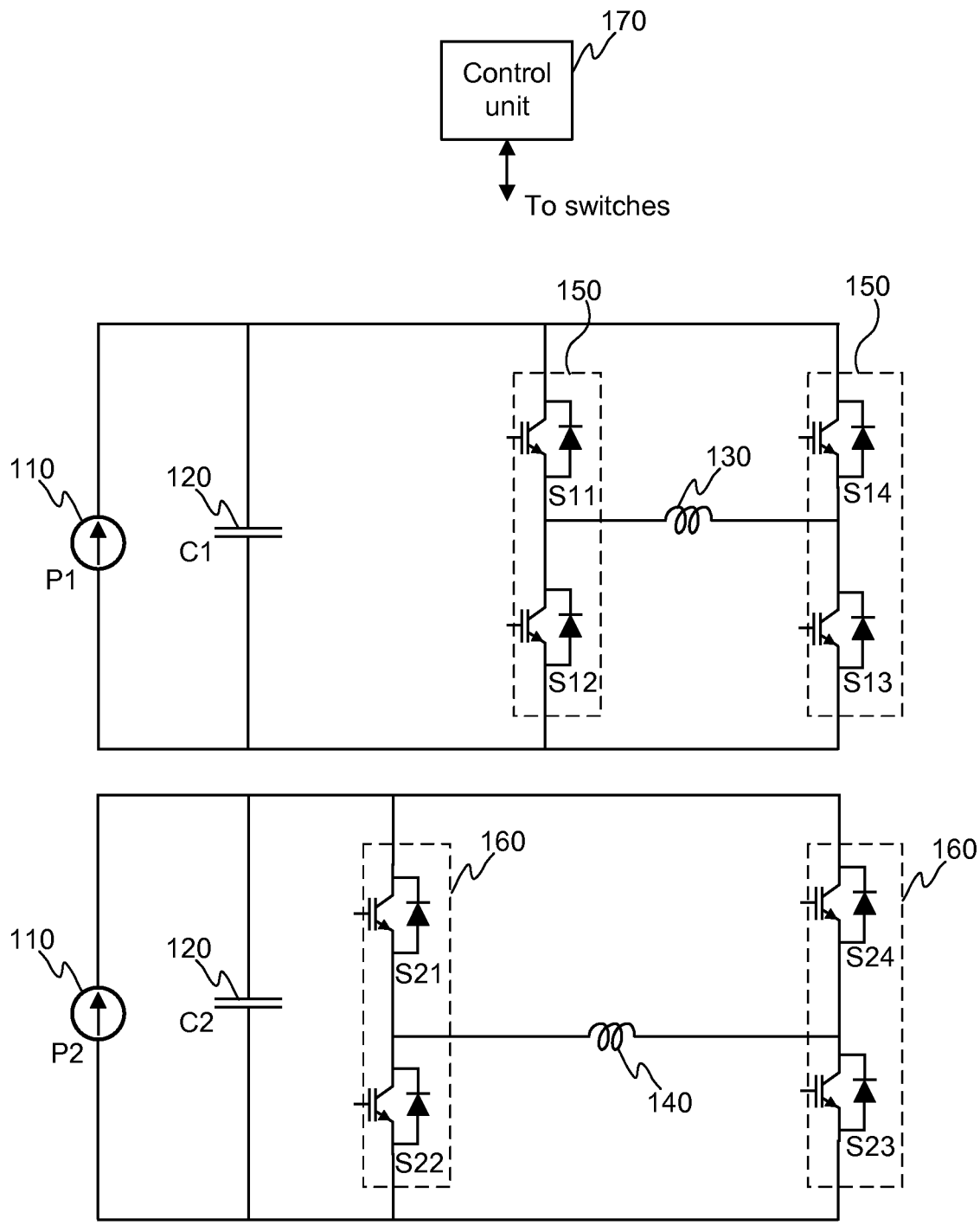
FIGS. 3A-3C schematically illustrate non-limiting examples of a device for multichannel transcranial magnetic stimulation according to the present invention.
Figure 3B:
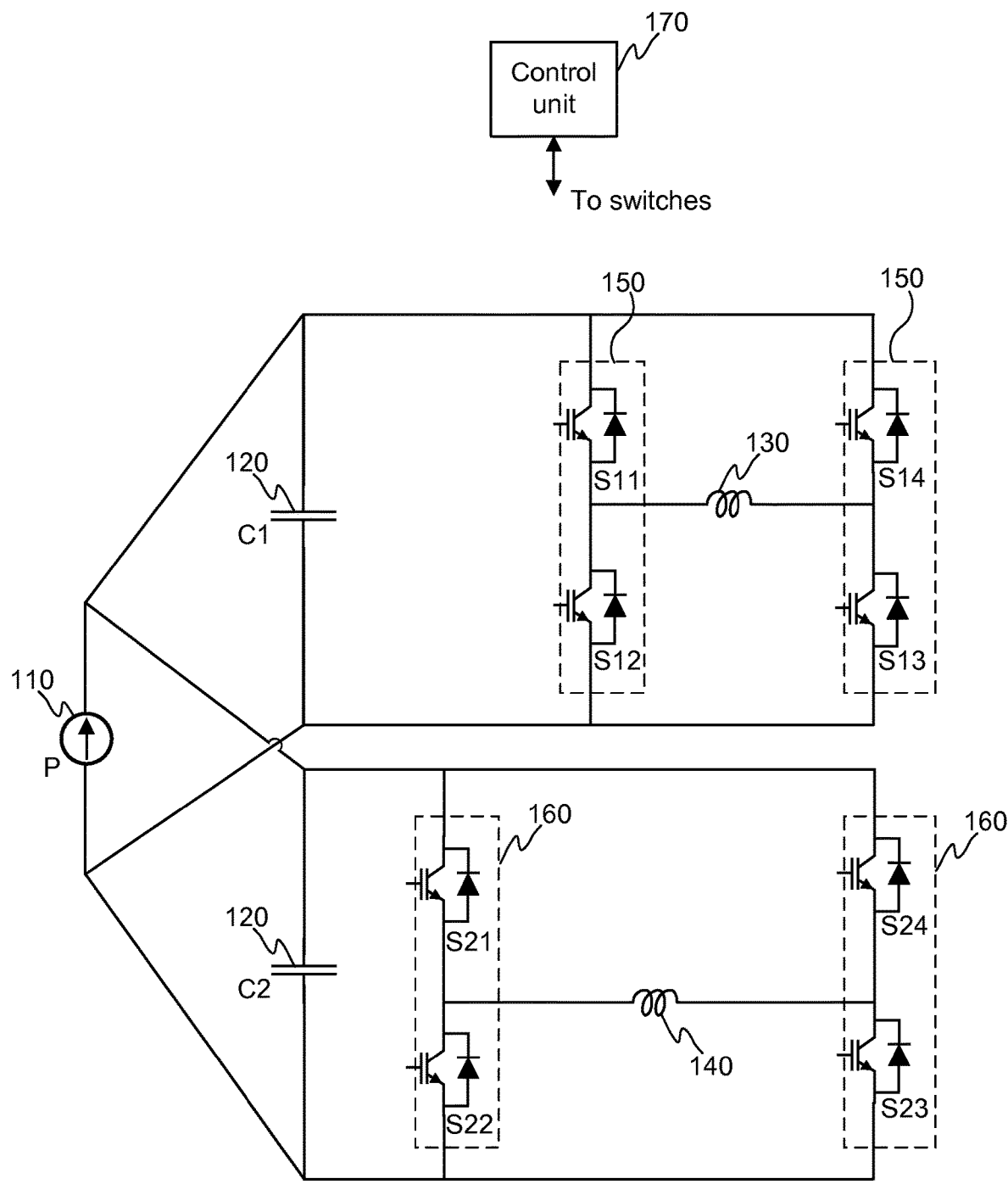
Figure 3C:
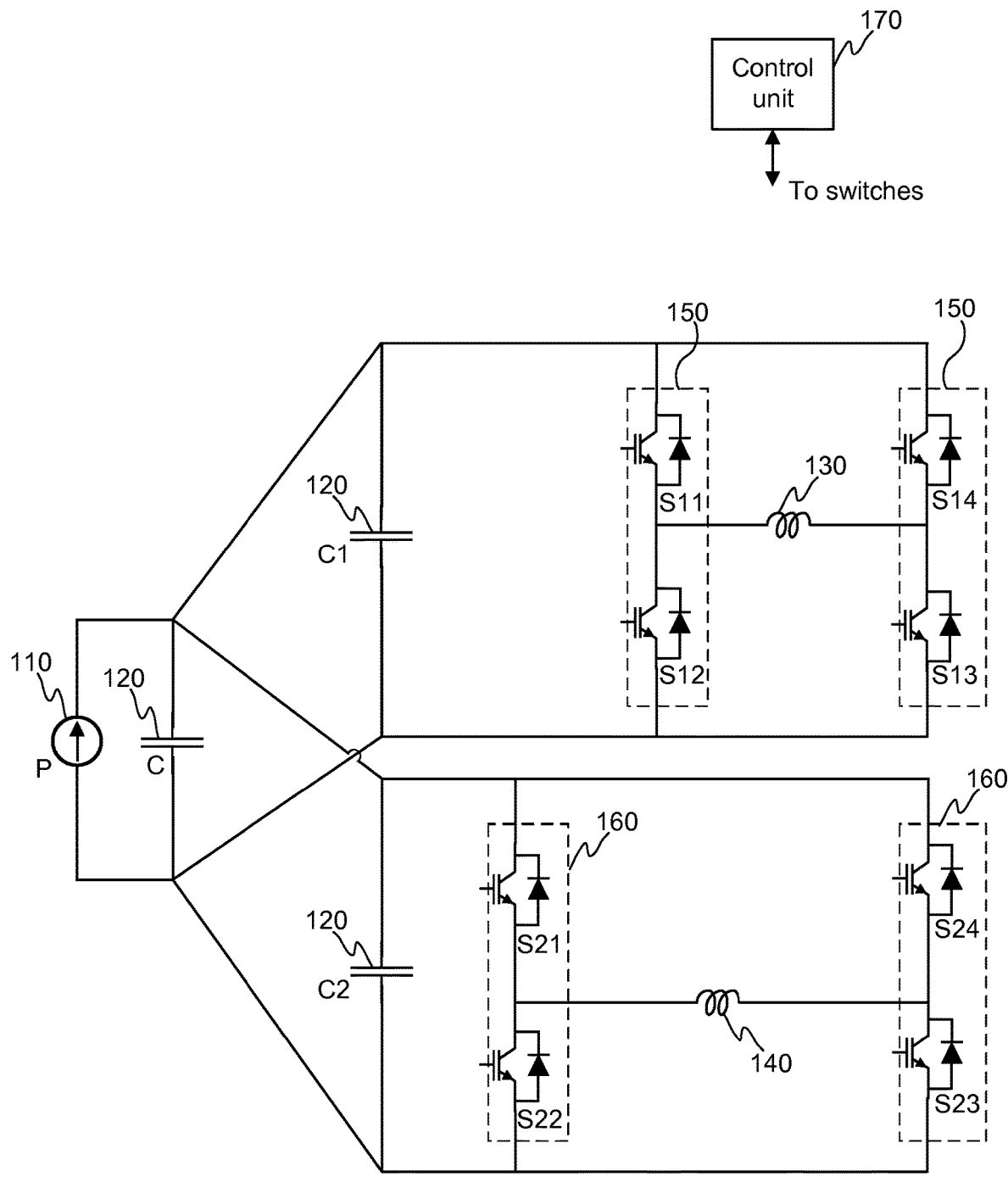

FIGS. 3A-3C schematically illustrate some non-limiting examples of an implementation of the device for multichannel transcranial magnetic stimulation in which there is either a dedicated energy storage for each coils (FIGS. 3A and 3B) or a combination of a dedicated energy storage and a common energy storage (FIG. 3C).

FIG. 3A schematically illustrates a solution wherein the device is implemented with two separate circuits in such a manner that a control unit 170 is configured to control the input channels 150, 160 in each circuit. In other words, for each coil 130, 140 it is arranged an own power source 110 (marked P1, P2), an own energy source 120, depicted as capacitors C1 and C2 in FIG. 3A and an own input channel 150, 160. The control unit 170 is coupled to the input channels 150, 160 and specifically to switching devices therein so that it may control the conductive state of the switching devices according to the modulation scheme.

FIG. 3B schematically illustrates another solution wherein the device implemented with a common power source 110, but for each coil 130, 140 a dedicated energy storage 120, such as a capacitor C1, C2, is arranged together with input channel 150, 160. Although not shown in FIG. 3B, in some embodiments, the power source 110 may be disconnected from the energy storages 120, and connected to one of them at a time with applicable coupling means, such as controllable switches, so that the energy levels of the energy storages C1 and C2 may be adjusted independently of each other.

In FIG. 3C it is schematically illustrated a still further example of an implementation of the device for a multichannel transcranial magnetic stimulation. The example in FIG. 3C comprises an energy storage array consisting of storages 120, wherein one energy storage C is common to both coils 130, 140 and in addition to that there are dedicated energy storages C1 and C2 for each coils 130, 140 that may be located e.g. physically close to the input channels 150, 160, respectively. The energy storages 120 are depicted as capacitors in FIG. 3C as also in FIGS. 3A and 3B. Each of energy storages 120 may consist of a further storage arrays in any of examples illustrated.

By selecting the characteristics of the energy storages in the embodiments of the inventions optimally further advantages may be achieved. For example, in the case that the energy storages are implemented with capacitors e.g. in the example as illustrated in FIG. 3C it is possible to obtain reduced stray inductance compared to the implementation of FIG. 2 by selecting the capacitances of the capacitors C1 and C2 smaller than the capacitance of the common capacitor C. The difference is especially emphasized when the number of channels is larger than two (as the total system capacitance must be large enough for all channels, and as there will be geometrical constraints in placing the different channels around a single capacitor). The wiring between C, C1, and C2 may or may not contain additional components, e.g., inductive parts that affect the circuit behavior. The other components depicted in FIG. 2 correspond to the ones depicted in FIG. 2.

The examples of FIGS. 2 and 3A-3C only show relevant elements needed for achieving at least some of the advantages of the present invention. They do not necessarily disclose all elements of a multichannel transcranial magnetic stimulation device. As mentioned, the implementations of the circuits in FIGS. 2 and 3A-3C are non-limiting examples for describing at least some aspects of the present invention. For example, in addition to the power source 110 the circuits may comprise means for discharging the energy storages. These means may comprise, e.g., resistors or IGBTs.

Figure 4A:
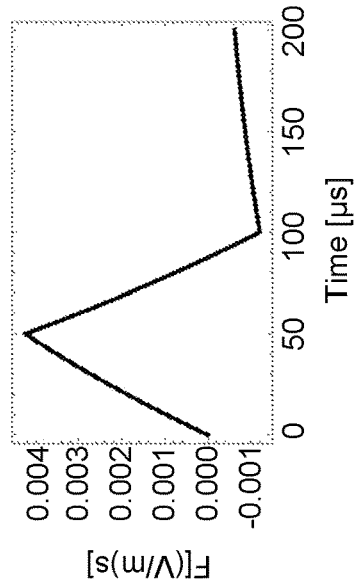
FIGS. 4A-4C schematically illustrate input and output signals of conventional devices.
Figure 4B:
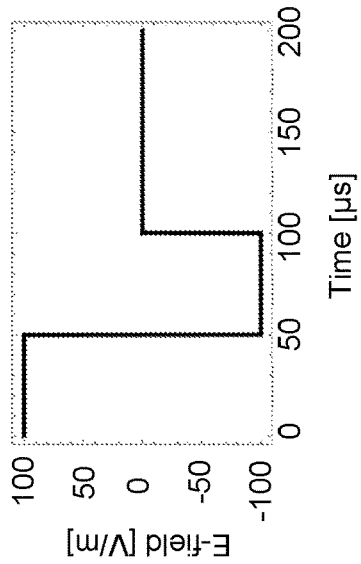
Figure 4C:
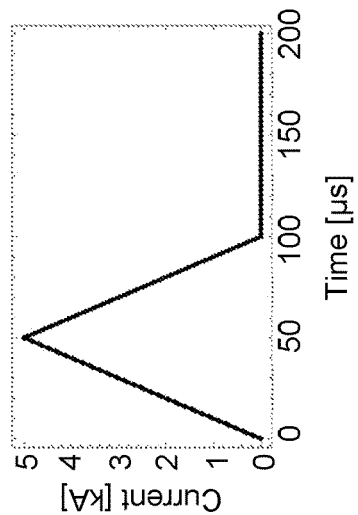

Next, at least some aspects relating to utilization of the solution according to the present invention in the multichannel transcranial magnetic stimulation are discussed. Here, the pulse modulation is considered first for the simplest case of ideal half-sine stimulation with a triangular current (assuming a large capacitance for the sake of simplicity of discussion and graphics). Namely, the effective stimulus location and intensity may be controlled by modulating the coil-current waveforms, and thus also the induced E-field waveforms, during the stimulus pulse. This pulse modulation of the induced E-field is achieved by interrupting the increase (or decrease) of the coil current for desired periods of time. The interruption may be achieved by controlling the conducting state of the switches belonging to the input channel of the coil in question, as discussed above. FIGS. 4A-4C schematically illustrate at least some aspects of conventional implementations in which a voltage of the energy storage must be adjusted in order to achieve a desired effect in the target. The stimulation of the target is achieved with triangular-pulse provided to a coil in question, wherein the coil current is ramped up and down passively in a monotonic way (FIG. 4A). Thus, the E-field is first positive and then negative as shown in FIG. 4B. The stimulus effect at the neuronal level in the target is shown in FIG. 4C, wherein it is assumed that the stimulus effect follows a model introduced by Barker et al. (1991) in which the effect of transcranial magnetic stimulation may be quantified by the parameter:

$$F(t) = \int_{-\infty}^{t} E(s)\exp\left(-\frac{t-s}{\tau}\right)ds,$$

wherein

E(s) is an E-field induced in the target, t is time, s is an integration variable and τ is a cellular or membrane time constant describing the relaxation of the membrane voltage towards its equilibrium.

As may be seen from the FIG. 4C if the stimulus intensity was to be changed (increased/reduced), the capacitor voltage must be adjusted, as the stimulus-intensity control was achieved by scaling the E-field intensity (which is proportional to the rate of change of the current).

Figure 5A:
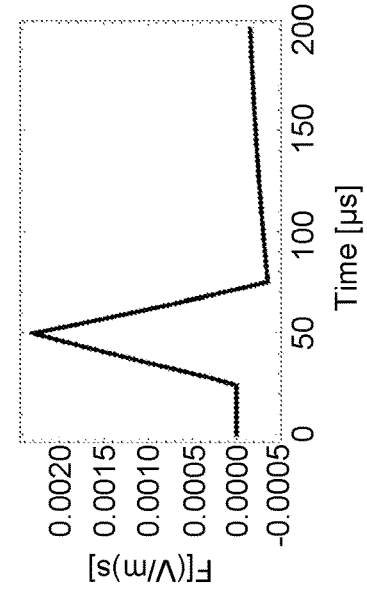
FIGS. 5A-5C schematically illustrate examples of input and output signals of an embodiment of the invention.
Figure 5B:
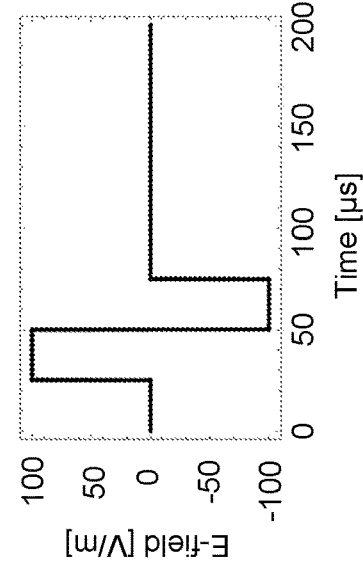
Figure 5C:
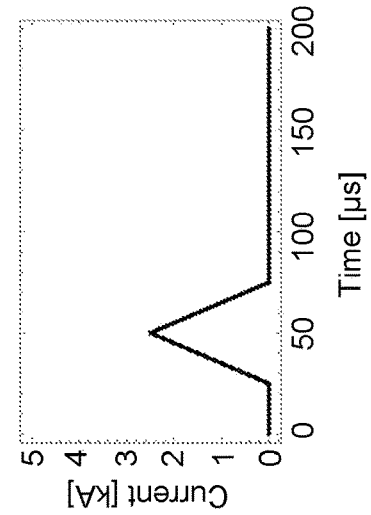

On the contrary, FIGS. 5A-5C disclose the effect achievable with a solution according to the present invention. Here, the control of the effective stimulus intensity, as shown in FIG. 5A, is at least in part achieved by reversing the rising current when it has reached, in this case, half of the maximum value of the pulse shown in FIG. 4A. As a consequence, the E-field duration is reduced to half of its original length. It shall be noted that the maximum E-field intensity (FIG. 5B), which is determined by the capacitor voltage that controls the rate of change of the current, is unchanged. However, according to the low-pass-filter model such as the equation by Barker et al. above this kind of a current reduces the membrane polarization or the effective stimulus intensity (cf. FIG. 5C) to approximately half of that in FIG. 4C.

However, as the total stimulus duration of the pulse shown in FIGS. 5A-5C is now reduced to half of the pulse shown in FIG. 4A-4C, this shortening of the pulse may have some non-trivial side effects, when neuronal populations with different time constants are present, or when the pulse duration is long compared to the membrane or cellular time constant. In other words, for neurons with short time constants, the longer pulse of FIG. 4A achieved with conventional solutions may lead to saturation that may not happen with the waveform of FIG. 5A. According to the present invention, this limitation may be overcome by making the stimulus waveforms to have (approximately) the same duration by using an in-pulse modulation consisting of multiple steps, as will be discussed next.

As indicated above by means of the present invention effective stimulus intensity may be changed by controlling the current flow suitably i.e. the input channel with the control signal, such as in a step-like manner. This produces an E-field time course with a characteristic in-pulse modulation. This reduces the stimulus effect to half of its original value without any need to change the energy storage voltage level, which may be the capacitor voltage level, as is needed to be done with conventional solutions. By varying the relative amount of the on- and off-states of the E-field (or by adding intervals with a decreasing current, i.e., negative E-field), the effective stimulus intensity may be altered in a wide range of values in a continuous manner. By adjusting the capacitor voltage so that the strongest pulses require some modulation, the stimulus intensity may be also increased by reducing the flat-current portions. This kind of approach enables sharing the energy storage between at least two coils.

Figure 6A:
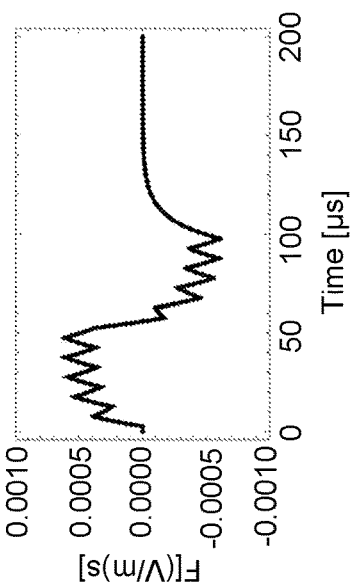
FIGS. 6A-6C schematically illustrate some further examples of input and output signals according to another embodiment of the invention.
Figure 6B:
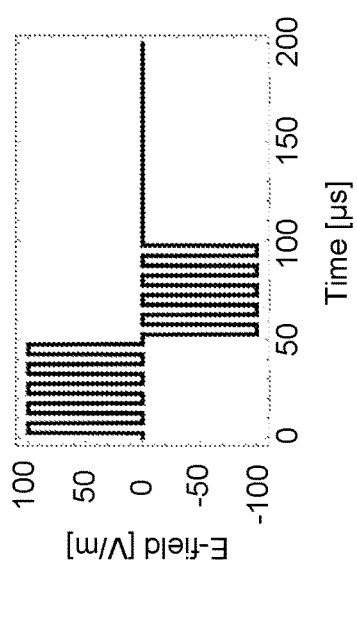
Figure 6C:
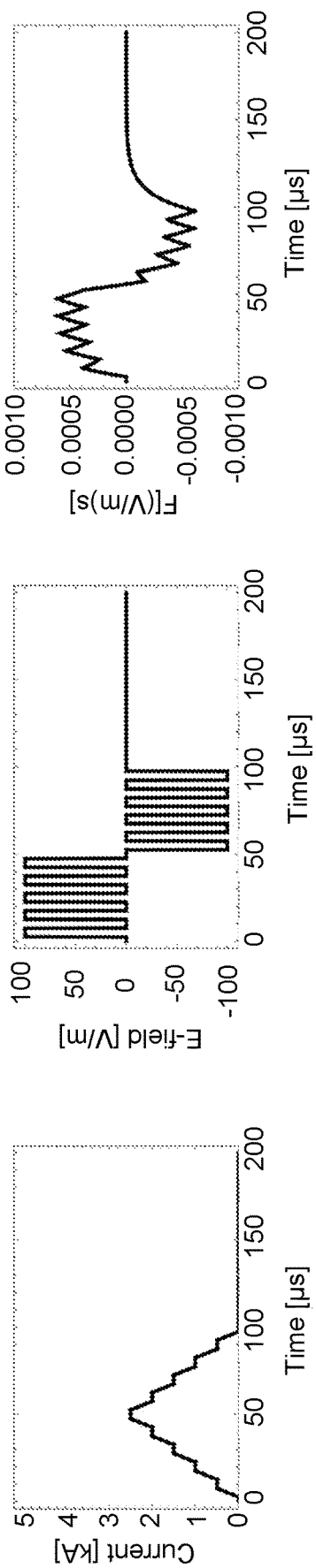

For clarifying the previous paragraph and the operation of the present invention it is referred to FIGS. 6A-6C wherein the FIG. 6A discloses a step-like increase and decrease of the current input to the coil under use. The step-like waveform of the current refers to a form which may contain several steps interrupted by near-constant segments. The input of the current in the step-like manner may be achieved by modulating the current output from the energy storage 120. The modulation may be achieved by controlling the switches in the input channels 150, 160 with an applicable control signal, or signals, generated by the control unit 170. The step-wise increase and decrease of the input current to the coil 130, 140 causes the E-field to oscillate between the zero level and the maximum level (when the current is increasing) and the minimum level (when the current is decreasing) as shown in FIG. 6B. The E-field generates the effective stimulus intensity (F) according to the FIG. 6C. In this manner it is possible to optimize the maximum current amplitude as well as to scale the effective stimulus intensity so that a saturation of the target, such as neurons, may be at least in part avoided. For sake of clarity it is worthwhile to mention that the accuracy of the stimulus intensity may be controlled by selecting necessary number of steps to the current waveform generated through modulation.

In some cases, it may be beneficial to use two (or several) charge-storage capacitors for each channel as the energy storage for TMS coils: one charged to a high voltage and another one to a lower voltage (requiring also a lower voltage rating). These capacitors may then be connected to the coil or the input circuit (consisting of the IGBTs) dynamically as desired. This may be beneficial, e.g., when a high stimulus intensity needs to be converted to a low effective intensity, which would otherwise require a modulation with rapid back-and-forth transitions (long off periods and very short on periods). With multiple capacitors with different voltage levels, the low-range stimulus intensities are best achieved by connecting the coil to the capacitor(s) with a low voltage level and by modulation the pulse waveform.

As mentioned, the present invention gives the possibility for multiple channels to share a common energy storage, such as a charge-storage capacitor, which may reduce the size and cost of the device. The invention allows using the same voltage level for multiple channels, which by in-pulse modulation may be converted to the desired individual effective intensity in each channel. Specifically, in mTMS use the invention provides means to rapidly change the stimulation target by feeding different channels with their own pulse modulations.

The modulation patterns described in the context of the previous figures are non-limiting examples. For example, the modulation pattern may also be time-varying, i.e., the in-pulse modulation may be denser in some parts of the pulse and less frequent in others. Also, although the example waveforms here started by having a zero current for a few microseconds (as compared to the original waveform), the waveform may as well start with a rising slope. The presented in-pulse modulation may be applied to any desired pulse waveform, including mono- and biphasic waveforms. A decrease or increase in the capacitor voltage level during a stimulation session, a finite capacitance, or other non-idealities may be compensated for by adjusting the in-pulse modulation accordingly. By further controlling the effective stimulus waveform as a function of time with a more advanced modulation, one can design pulses that allow optimally measuring the membrane or cellular time constants, e.g., by using simultaneous electroencephalography (EEG) or electromyography (EMG) recordings. The stimulus waveform may also be modulated in a way that minimizes the stimulus artefacts in combined recordings. Furthermore, the waveforms and pulse modulation schemes may be different in different channels.

The model and its parameters used above when describing the aspects of the present invention may be derived from electromagnetic and physiological theory, from results of measurements, or from their combination; the model may, e.g., be based solely on experimental observation of the stimulation outcome or be based on simulations. The model and its parameters may be different from the ones used above.

Furthermore, the present invention allows one to totally avoid the charging artefact that may occur in physiological (e.g., EEG or EMG) or other type of measurements (e.g., sound or video recording) that are performed together with TMS. Especially, in mTMS use, the artefact may otherwise disturb the interpretation of the measured signals, when some voltage adjustments would be needed within a pulse train.

As discussed already the input channel 150, 160 comprises such switching elements, or components, which are applicable in the context of mTMS. For example, IGBT devices may be used, but any other components suitable for switching or adjusting strong currents may be used, such as MOSFETs. The control of the coil currents may be combined with knowledge of the physical movement of the coil(s) or the movements of the head or other target tissue so as to achieve the desired E-field spatial pattern in the target area. The modulation patterns or sequences of patterns to achieve a desired effective stimulation may e.g. be predetermined and loaded from a storage media accessible for the control unit 170 when needed or the modulation pattern can be computed when needed. The computation may involve optimization of the waveform or it may be achieved without optimization. Moreover, the modulation pattern may also be at least in part dependent on the energy level of the energy storage 120 that may be common to the plurality of coils 130, 140.

The effective E-field and the coil currents may be controlled by a pulse-width-modulation (PWM) control of the input channels, i.e. the switching devices, such as IGBTs, therein, generated by the control unit 170 in which the flat/rising/descending parts of the current waveform may be shorter than the duration of the pulse. However, the effective E-field and coil currents may also be designed to be non-PWM type. In this case, the stimulus effect and/or location may be controlled by varying, e.g., the total duration of the stimulus waveforms that may or may not be of a triangular/sinusoidal shape.

The driving electronics of the coils, as already indicated, may consist of a single circuit of, e.g., 2 or 4 main IGBTs and 1 or 2 charge-storage capacitors, or it may be built in a modular fashion so that a collection of capacitor are connected/disconnected from the circuit with their own IGBTs when needed. This kind of approach allows controlling the pulse waveform in a more detailed manner by varying the number of capacitors and the set of capacitors that are connected to the coil as a function of time or on the basis of the desired effective stimulation outcome. The controlling of the chosen energy storages, such as capacitors, may be synchronous or asynchronous.

Figure 7:
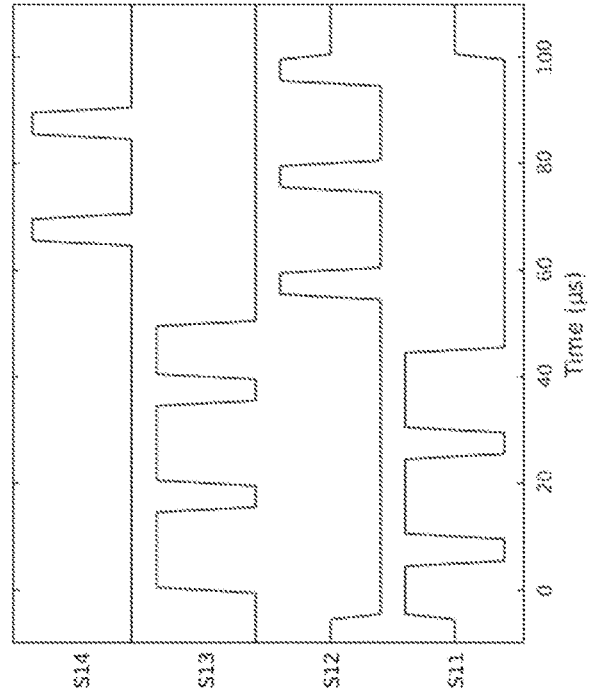
FIG. 7 schematically illustrates an example of control signals provided to switching devices of a transcranial magnetic stimulation device according to an embodiment of the invention.

In FIG. 7 it is schematically illustrated an example of control signals generated by the control unit 170 in order to generate the modulation pattern as shown in FIG. 6 with the circuit implementation as illustrated in FIG. 2. FIG. 7 illustrates the control signals to be input to the switches S11, S12, S13, and S14 to create the modulation pattern shown in FIG. 6 used for controlling an input of the current to the coil 130 in the circuit implementation of FIG. 2. Similarly, the control unit 170 may be configured to generate control signals to other switches in any circuit implementation according to the present invention, such as switches S21, S22, S23 and S24 in the implementation of FIG. 2.

Figure 8:
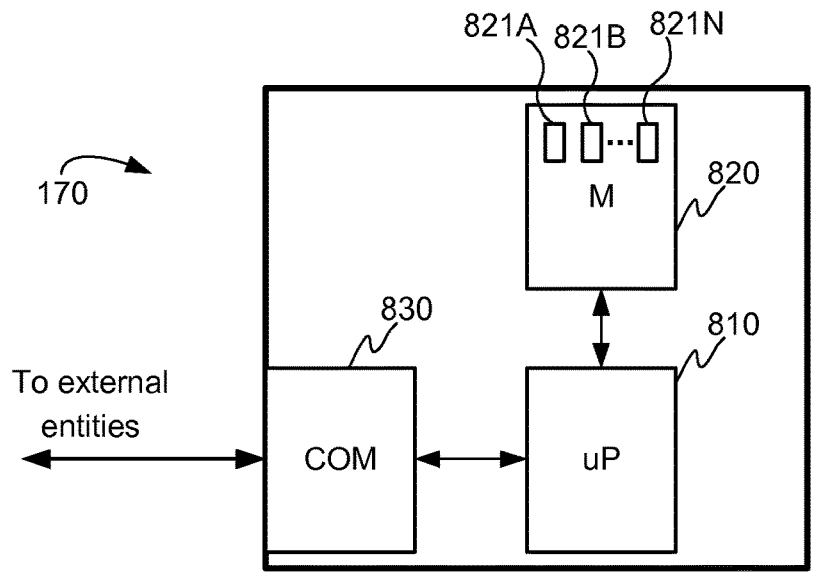
FIG. 8 schematically illustrates a control unit of a transcranial magnetic stimulation device according to an embodiment of the invention.

FIG. 8 schematically illustrates a control unit 170 according to an example of the invention. The control unit 170 may be configured, at least in part, to implement at least some functions of the present invention as described. This may be achieved by arranging a processor 810 forming a processing unit in this example to execute at least some portion of computer program code 821A-821N stored in a memory 820 causing the processor 810, and, thus, the control unit 170 to implement one or more functions as described. Thus, the processor 810 may be arranged to access the memory 820 and retrieve and store any information therefrom and thereto. Moreover, the processor 810 may be configured to control communication through a communication interface 830 with any external unit, such as with at least one input channel and possibly with any other entity, such as with a device suitable for providing information on energy level of the energy storage common to a plurality of coils. In other words, the control unit 170 may be communicatively coupled to at least some of the mentioned entities either directly or indirectly. The processor 810 may also be configured to control overall operability of mTMS device according to instructions stored in the memory 820 in a form of computer program code and parameters thereto. For sake of clarity, the processor herein refers to any unit suitable for processing information and control the operation of the control unit 170 in achieving a desired operation as described. The mentioned operations may e.g. be implemented with a microcontroller solution with embedded software. Similarly, the invention is not limited to a certain type of memory only, but any memory type suitable for storing the described pieces of information may be applied in the context of the present invention. The present invention is described above so that the functions are implemented in one control unit 170 only. However, the implementation may also be done in a decentralized manner i.e. between multiple control units that are operatively coupled to each other either directly or indirectly for achieving desired functions. Among the other possible tasks the control unit 170 as schematically illustrated in FIG. 8 is advantageously configured to generate control signals for controlling the modulation of the input current to the coil 130, 140. The control signals may refer to signals by means of which it is possible to control conducting states of the switches belonging to the input channel(s) of the device.

Figure 9:
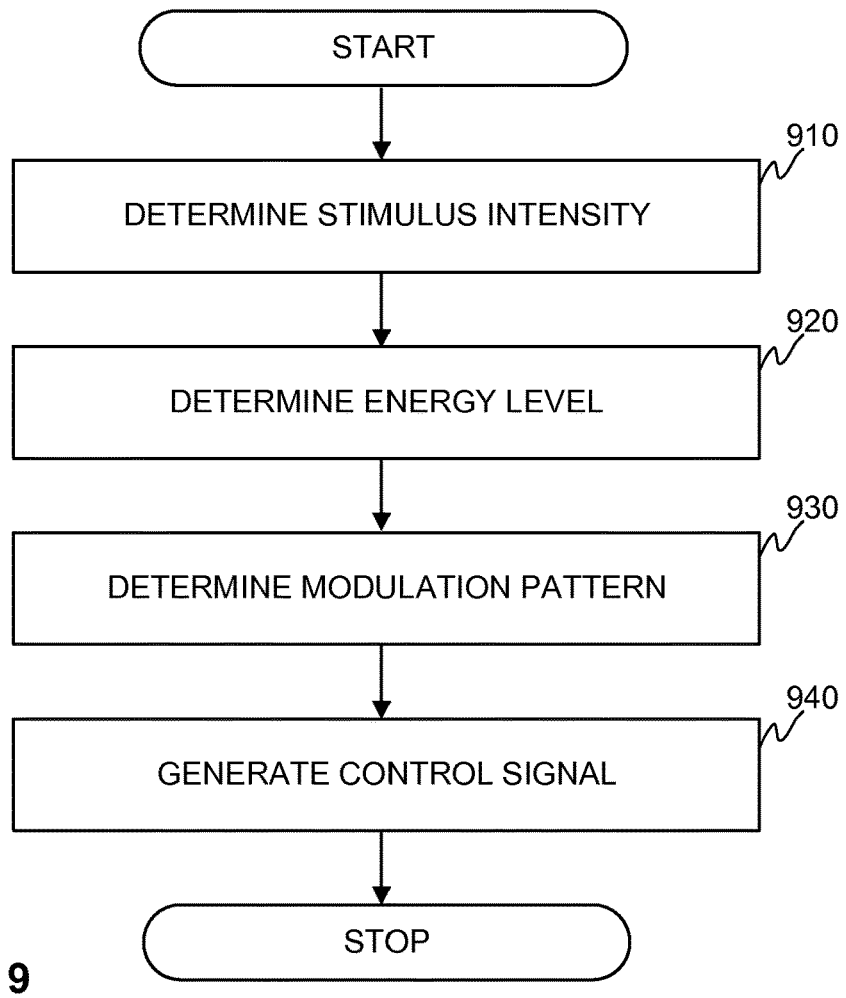
FIG. 9 schematically illustrates a method according to an embodiment of the invention.

Some aspects of the present invention may relate to a method as schematically illustrated in FIG. 9. The method enables at least in part controlling an input of a plurality of coils of a transcranial magnetic stimulation device as described. The method may comprise the following steps: determining at least one stimulus intensity 910 intended to be generated in the target by generating magnetic field by at least one coil of the at least two coils; determining an energy level 920 stored in the at least one energy storage; determining a modulation pattern 930 for each coil for generating the magnetic field by the at least one coil of the at least two coils, the generated magnetic field by the at least one coil causing the intended stimulus intensity in the target; generating at least one control signal 940 for controlling the input channel of the at least one coil of the at least two coils according to the determined modulation pattern in order to control an input of each coil from the at least one energy storage. In some embodiments of the invention, the order of these steps may differ from that shown in FIG. 9.

The present invention enables performing paired-pulse stimulation (or short bursts of stimuli) sequences where the second pulse is equally strong or stronger than the first pulse (or the desired ones of the latter pulses are). Any of the subsequent pulses may also be made weaker than the first pulse. Further, these may be performed without any intermediate charging or discharging, and thus without charging-associated artefact in, for example, EEG signal. Also, as mentioned, in the multichannel TMS it is possible to adjust individual-channel stimulus amplitudes programmatically without need to charge and/or discharge the capacitors. This makes it easier to perform, for example, coil-movement correction for multichannel TMS. Further, the present invention allows avoidance of the charging artefact that may occur in physiological (e.g., electroencephalography (EEG) or electromyography (EMG)) or other type of measurements (e.g. sound or video recording) that are performed together with TMS. Especially, in mTMS use, the artefact may otherwise disturb the interpretation of the measured signals, when some voltage adjustments would be needed within a pulse train.

In the description herein, at least one energy storage 120 may be arranged for each coil 130, 140 in a plurality of ways as already mentioned. There may be either at least one common energy storage 120 for a plurality of coils 130, 140. Alternatively, there may be arranged at least one dedicated energy storage 120 for each coil 130, 140. In addition, it is possible to arrange at least one energy storage so that there is at least one common energy storage 120 for the coils 130, 140 and additionally at least one dedicated energy storage 120 for at least some of the coils 130, 140. Still further, one possible arrangement may be that at least one common energy storage 120 is provided for a plurality of coils 130, 140 and at least one dedicated energy storage 120 is provided for at least one coil 130, 140 in the device.

In the description herein the term "target" shall be understood to cover any object, or some portion of an object, into which stimulation is intended to be generated. Some non-limiting examples of the target may e.g. be a brain or only some portion of the brain, a skull or even a specific point in the brain.

The specific examples provided in the description given above should not be construed as limiting the applicability and/or the interpretation of the appended claims. Lists and groups of examples provided in the description given above are not exhaustive unless otherwise explicitly stated.

The invention claimed is:

1. A transcranial magnetic stimulation device comprising:
at least two coils,
an input channel for each coil,
a control unit, and
at least one energy storage for storing energy for the at least two coils,
wherein the control unit is configured to:
determine at least one stimulus intensity intended to be generated in a target by generating a magnetic field by at least one coil of the at least two coils,
determine an energy level stored in the at least one energy storage,
determine a modulation pattern individually for each coil, the modulation pattern being at least in part dependent on the energy level of the at least one energy storage, for generating the magnetic field by the at least one coil of the at least two coils, the generated magnetic field by the at least one coil causing the intended stimulus intensity in the target, and
generate at least one control signal for controlling the input channel of the at least one coil of the at least two coils according to the determined modulation pattern in order to control an input of the at least one coil of the at least two coils from the at least one energy storage.

2. The transcranial magnetic stimulation device of claim 1, wherein the at least one energy storage is arranged in one of the following manners: (i) the at least one energy storage comprises at least one common energy storage for a plurality of the coils, (ii) the at least one energy storage comprises at least one dedicated energy storage for each coil, (iii) the at least one energy storage comprises at least one common energy storage for a plurality of the coils and at least one dedicated energy storage for each coil, or (iv) the at least one energy storage comprises at least one common energy storage for a plurality of the coils and at least one dedicated energy storage for at least one coil of the plurality of the coils.

3. The transcranial magnetic stimulation device of claim 1, wherein the at least one energy storage comprises at least one capacitor.

4. The transcranial magnetic stimulation device of claim 1, wherein the control unit is further configured to determine the energy level stored in the at least one energy storage by measuring a voltage level of the at least one energy storage.

5. The transcranial magnetic stimulation device of claim 1, wherein the control unit is configured to, in response to a detection that the energy level stored in the at least one energy storage is below an energy level needed for generating a magnetic field with the at least one coil causing the intended stimulus intensity in the target with the determined modulation pattern, initiate a charging of the at least one energy storage.

6. The transcranial magnetic stimulation device of claim 1, wherein the control unit is configured to determine the modulation pattern for generating a plurality of consecutive magnetic fields with the at least one coil.

7. The transcranial magnetic stimulation device of claim 1, wherein the generated at least one control signal is configured to control a conductive state of at least one switching device in the input channel of the at least one coil of the at least two coils.

8. The transcranial magnetic stimulation device of claim 7, wherein the at least one switching device is at least one of the following: insulated-gate bipolar transistor, IGBT; or metal-oxide-semiconductor field-effect transistor, MOSFET.

9. The transcranial magnetic stimulation device of claim 1, wherein the control unit is configured to control the input of each coil with a pulse-width-modulation-based control signal.

10. The transcranial magnetic stimulation device of claim 1, wherein the control unit is configured to control the input of each coil in a step-like manner.

11. A method for controlling an input of a plurality of coils of a transcranial magnetic stimulation device comprising:
at least two coils,
an input channel for each coil,
a control unit, and
at least one energy storage for storing energy for the at least two coils,
wherein the method comprises:
determining at least one stimulus intensity intended to be generated in a target by generating a magnetic field by at least one coil of the at least two coils, determining an energy level stored in the at least one energy storage, determining a modulation pattern individually for each coil, the modulation pattern being at least in part dependent on the energy level of the at least one energy storage, for generating the magnetic field by the at least one coil of the at least two coils, the generated magnetic field by the at least one coil causing the intended stimulus intensity in the target, and generating at least one control signal for controlling the input channel of the at least one coil of the at least two coils according to the determined modulation pattern in order to control an input of the at least one coil of the at least two coils from the at least one energy storage.

\* \* \* \* \*